United States Patent [19]

Devon et al.

[11] Patent Number: 4,960,949

[45] Date of Patent: Oct. 2, 1990

[54] LOW PRESSURE RHODIUM CATALYZED HYDROFORMYLATION OF OLEFINS

[75] Inventors: Thomas J. Devon; Gerald W. Phillips; Thomas A. Puckette; Jerome L. Stavinoha; Jeffrey J. Vanderbilt, all of Longview, Tex.

[73] Assignee: Eastman Kodak Company, Rochester, N.Y.

[21] Appl. No.: 288,596

[22] Filed: Dec. 22, 1988

[51] Int. Cl.$^5$ ............................................. C07C 45/50
[52] U.S. Cl. ...................................... 568/454; 556/16; 556/136; 568/451
[58] Field of Search .................. 568/451, 454; 556/16, 556/136

[56] References Cited

U.S. PATENT DOCUMENTS

| | | | |
|---|---|---|---|
| 3,239,566 | 3/1966 | Slaugh et al. | 260/604 |
| 3,527,809 | 9/1970 | Pruett et al. | 260/604 |
| 4,138,420 | 2/1979 | Unruh et al. | 260/439 |
| 4,152,344 | 5/1979 | Unruh | 260/439 |
| 4,215,077 | 7/1980 | Watsumoto et al. | 568/454 |
| 4,277,627 | 7/1981 | Bryant et al. | 568/454 |
| 4,370,258 | 1/1983 | Ogata et al. | 252/429 |
| 4,605,781 | 8/1986 | Tau | 568/454 |
| 4,694,109 | 9/1987 | Devon et al. | 568/454 |
| 4,742,178 | 5/1988 | Nelson et al. | 568/454 |
| 4,755,624 | 7/1988 | Phillips et al. | 568/454 |
| 4,760,194 | 7/1988 | Phillips et al. | 568/454 |

FOREIGN PATENT DOCUMENTS 2014138 8/1979 United Kingdom ............... 568/454

OTHER PUBLICATIONS

Pruett and Smith, Journal of Organic Chemistry, vol. 34, pp. 327–330 (1968).
Pittman and Hirao, Journal of Organic Chemistry, vol. 43, pp. 640–646 (1978).
Hayashi et al., Bulletin of the Chemical Society of Japan, vol. 54, pp. 3438–3446 (1981).

*Primary Examiner*—Werren B. Lone
*Attorney, Agent, or Firm*—J. Frederick Thomsen; S. E. Reiter; William P. Heath, Jr.

[57] ABSTRACT

The hydroformylation of olefins with rhodium complex catalysts is described. The catalysts employed comprise a rhodium complex with at least one bidentate ligand having a specified structure,

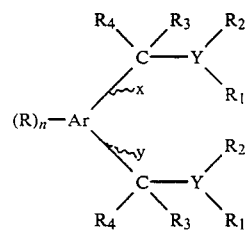

Hydroformylation reactions at relatively low temperatures and pressure and yet with high rates of reaction and high selectivity to aldehyde product are obtained by the practice of the present invention.

19 Claims, No Drawings

LOW PRESSURE RHODIUM CATALYZED HYDROFORMYLATION OF OLEFINS

This invention relates to the rhodium catalyzed hydroformylation of olefins.

BACKGROUND OF THE INVENTION

It is well known in the art to convert olefins to aldehydes having one additional carbon atom by contacting the olefin with hydrogen and carbon monoxide in the presence of a catalyst based on cobalt or rhodium metal. Rhodium-based catalysts have the advantage, relative to cobalt-based catalysts, of being able to promote the hydro-formylation of olefins under less severe operating conditions.

One disadvantage of prior art rhodium-based catalysts is the propensity of such materials to lose activity over a Period of time as a result, for example, of ligand decomposition. Triaryl phosphines, for example, are prone to conversion into alkyl diaryl phosphines under hydroformylation reaction conditions. These alkyl diaryl phosphines as rhodium ligands give lower activity catalysts compared to the triaryl phosphines.

Another disadvantage of prior art rhodium-based catalysts is the fact that not all rhodium salts are suitable starting materials for the preparation of rhodium complexes. For example, it is frequently observed that a several hour induction period is required to transform the rhodium complexes into active hydroformylation catalysts. This problem is particularly acute when halide containing compounds of rhodium are employed for the preparation of rhodium complexes.

Yet another disadvantage of rhodium-based catalyst systems is the high cost of the rhodium metal employed for catalyst preparation. Where one employs low levels of rhodium metal in order to reduce catalyst costs, low reaction rates frequently result.

There is, therefore, a continuing need in the field for high activity, high selectivity rhodium-based hydroformylation catalyst systems.

There is also a continuing need in the field for selective catalyst systems for the hydroformylation of alpha olefins. Catalyst systems which are tailored to prepare aldehyde products having specific linear to branched chain isomer ratios would be particularly valuable. Those of skill in the art recognize that there is substantial potential market for derivatives of branched chain aldehydes, as well as the existing large market for linear aldehyde hydroformylation products.

Current commercial scale hydroformylation plants based on high pressure cobalt carbonyl catalyst systems produce marketable quantities of both linear and branched chain aldehydes. The presently preferred, low pressure hydroformylation employing rhodium-based catalyst systems, e.g., triphenyl-phosphine-rhodium complex, typically produce aldehyde products with a high selectivity to linear product. Thus, such catalyst systems do not increase the availability of desirable branched-chain aldehyde products.

Other rhodium-based hydroformylation catalyst systems, e.g., tricyclohexylphosphine-rhodium complex or dicyclohexylphenylphosphine-rhodium complex, produce aldehyde product mixtures with very low linear to branched chain isomer ratios. Indeed, such catalyst systems frequently have lower selectivity to linear product than do the high pressure cobalt-based catalyst systems. Therefore, a catalyst system capable of operating at low pressure while producing linear to branched-chain product ratios comparable to the ratios obtained with high pressure cobalt-based catalyst systems would be highly desirable Such a catalyst system would allow a commercial aldehyde producer to shift from an expensive high pressure process based on a cobalt catalyst system to a much less expensive low pressure process based on a rhodium catalyst system.

OBJECTS OF THE INVENTION

An object of the present invention, therefore, is a method for the rhodium promoted hydroformylation of olefins to produce aldehydes in high yield and at a high rate of conversion.

Another object of the present invention is a method for the rhodium-promoted hydroformylation of olefins to produce aldehydes in a highly selective reaction, i.e., with very low levels of by-product formation.

Yet another object of the present invention is a rhodium complex catalyst which remains stable and soluble for extended periods of time under hydroformylation conditions.

Still another object of the present invention is a method for the rhodium-promoted hydroformylation of olefins employing low levels of rhodium and low levels of ligand for the rhodium catalyst.

A further object of the present invention is a rhodium-based hydroformylation catalyst system capable of producing aldehyde products having a linear to branched chain isomer ratio comparable to that produced by high pressure cobalt promoted hydroformylation processes.

These and other objects of the present invention will become apparent from inspection of the detailed description and appended claims.

STATEMENT OF THE INVENTION

In accordance with the present invention, we have discovered high selectivity, high activity rhodium catalysts for use in the hydroformylation of olefins. High yields of hydroformylation products are obtained with very low levels of undesired by-products. These novel catalysts allow the hydroformylation of olefins to be carried out at low pressures with relatively low levels of rhodium catalyst and ligand therefor.

DETAILED DESCRIPTION OF THE INVENTION

In accordance with the present invention, we have discovered a class of hydroformylation reaction catalysts which give high yield of hydroformylation product with high selectivity. Such reactions are promoted by soluble rhodium catalysts complexed with phosphine ligands having the following generic formula

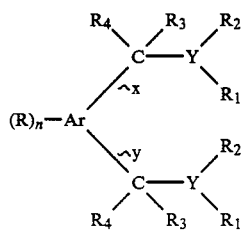

wherein

Ar is selected from aromatic ring compounds having 6 up to 14 carbon atoms, e.g., phenyl, naphthyl, phenanthryl and anthracenyl;

the x bonds and the y bonds are attached to adjacent carbon atoms on the ring structure;

each R, when present as a substituent, is independently selected from alkyl, alkoxy, aryloxy, aryl, aralkyl, alkaryl, alkoxyalkyl, cycloaliphatic, halogen (except Cl, Br or I on the aromatic nucleus on the carbon atom adjacent to the carbon atoms bearing the x and- /or y bonds), alkanoyl, alkanoyloxy, alkoxycarbonyl, formyl, carboxylate moieties, sulfonic acid derivatives, or amino moieties;

n is a whole number in the range of 0–4 where Ar is phenyl; 0–6 where Ar is naphthyl; and 0–8 where Ar is phenanthryl or anthracenyl;

each $R_1$ and $R_2$ is independently selected from alkyl, aryl, aralkyl, alkaryl, cycloaliphatic radicals and substituted derivatives thereof;

each $R_3$ and $R_4$ is independently selected from hydrogen and the $R_1$ substituents;

each of the above alkyl groups or moieties is straight or branched chain of 1–20 carbons, preferably 1–8 carbons;

each aryl group contains 6–10 ring carbons;

each cycloaliphatic group contains from 4–8 ring carbons; and each Y is independently selected from the elements P, As, Sb and Bi.

Substituted derivatives of $R_1$ and $R_2$ include substituents such as alkyl, alkoxy, aryloxy, aryl, aralkyl, alkaryl, alkoxyalkyl, cycloaliphatic, halogen, alkanoyl, alkanoyloxy, alkoxycarbonyl, formyl, carboxylate moieties, sulfonic acid moieties or amino moieties.

Exemplary compounds which satisfy this generic formula include:

α,α'-bis(diphenylphosphino)-o-xylene, (oxyl)
3,4-dichloro-α,α'-bis(diphenylphoshino)-o-xylene,
α,α'-bis[di(p-trrifluoromethylphenyl)phosphino]-o-xylene, and the like, as well as mixtures of two or more thereof.

Optionally, the invention bidentate ligand can be employed in combination with monodentate organophosphine ligands having the structure $PR^y_3$, wherein each $R^y$ is independently selected from alkyl, aryl, aralkyl, alkaryl, cycloaliphatic radicals and substituted derivatives thereof; and wherein substituted derivatives of $R^y$ include aralkyl, alkaryl, alkoxyalkyl, cycloaliphatic, halogen, alkanoyl, alkanoyloxy, alkoxycarbonyl, formyl, carboxylate moieties, sulfonic acid moieties or amino moieties. Exemplary monodentate organo-phosphine ligands include triphenylphosphine, tribenzylphosphine, benzyldiphenylphosphine, dibenzylphenylphosphine, tricyclohexylphosphine, diphenyl cyclohexylphosphine, diphenyl-n-butyl-phosphine, tris(3,4'-dichlorobenzyl)phosphine, tri(4-t-butylbenzyl)phosphine, and the like. The use of such mixtures tends to increase the catalyst productivity while having essentially no effect on the linear to branched chain isomer ratio of the aldehyde products.

When monodentate organophosphine ligands are employed, suitable monodentate ligand/rhodium molar ratios can vary widely. Broadly, from about 0.5 up to about 200 moles of monodentate ligand per mole of rhodium metal can be employed. Preferably, ratios in the range of about 1 up to 50 moles of monodentate ligand per mole of rhodium will be employed, with ratios in the range of about 2 up to 30 being most preferred.

Many sources of rhodium can be used as the rhodium component for preparation of the catalyst of the invention, provided that the source of rhodium employed can be converted into soluble carbonyl-ligand complexes of rhodium Suitable rhodium compounds include:

rhodium (I) dicarbonylacetonylacetonate,
rhodium (II) 2-ethylhexanoate,
rhodium (II) acetate,
rhodium (0) carbonyls (e.g., $Rh_6(CO)_{16}$, $Rh_4(CO)_{12}$),
$HRh(CO)(P_3P)_3$, where Ph=phenyl group as well as mixtures of any two or more thereof It is preferred that non halogen containing rhodium compounds be used to avoid problems of low catalyst activity caused by the presence of residual halide, to avoid the corrosive effects of residual halide ions, and the like. In addition, salts of strong mineral acids are desirably avoided as sources of rhodium because these compounds release acids which are detrimental to rhodium catalyst activity under hydroformylation conditions We have found rhodium 2-ethylhexanoate to be a particularly preferred source of rhodium from which to prepare the complex catalyst of the invention because it is a convenient source of soluble rhodium, as it can be efficiently prepared from inorganic rhodium salts such as rhodium halides.

No special provisions are required for the preparation of the catalyst employed in the practice of the present invention, although it is preferred, for high catalyst activity, that all manipulations of the rhodium and phosphine components be carried out under an inert atmosphere, e.g., $N_2$, Ar, and the like. The desired quantities of a suitable rhodium compound and ligand are charged to the reactor in a suitable solvent. The sequence in which the various catalyst components are charged to the reactor is not critical. Thus, the rhodium component can be added to the reactor, then the phosphine component; or conversely, the phosphine component can be added to the reactor, then the rhodium component; or, alternatively, the preformed rhodium phosphine complex can be charged to the reactor.

Suitable solvents, if one chooses to use solvent in the practice of the invention, include those which do not adversely affect the hydroformylation process and which are inert with respect to the catalyst, olefin, hydrogen and carbon monoxide feeds as well as the hydroformylation products. Inert solvents of this nature are well known to those of skill in the art and include such solvents as benzene, xylene, toluene, as well as their substituted derivatives; pentanes, naphtha, kerosene, mineral oils, cyclohexane, cyclopentane, ethers, esters, etheresters, alcohols, acetals, ketones, water, as well as various mixtures thereof preferred solvents are those which are sufficiently high boiling to remain, for the most part, in a gas sparged reactor, and include such compounds as 2,2,4-trimethyl 1,3-pentanediol monoisobutyrate (TMPDMI; available from the Eastman Chemicals Division of Eastman Kodak Company as Texanol ® solvent), and its isomers, as well as the by-products of the hydroformylation reaction, such as alcohols, esters, acetals and hydroxyaldehydes which are retained as high boiling liquids at the bottom of subsequent distillation columns.

The active catalyst produced by employing the above described starting materials and procedure is believed to consist primarily of compounds of the structure:

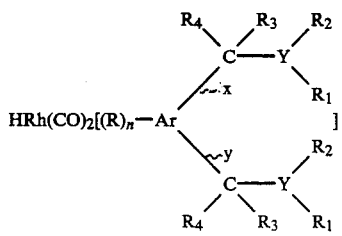

wherein Ar, Y, R, $R_1$, $R_2$, $R_3$, $R_4$, x, y and n are as previously defined.

The process of the present invention can be carried out with widely varied amounts of rhodium For example, amounts of catalyst containing as little as about $1 \times 10^{-6}$ moles of rhodium (calculated based on rhodium metal) per mole of olefin in the reactor zone can be employed. Such low catalyst concentrations are not generally commercially desirable since the reaction rates are frequently rather low. There is no upper limit as to operable catalyst concentrations, but such upper limit is generally determined by the high cost of rhodium metal and the fact that no advantage is generally obtained with catalyst amounts greater than about $1 \times 10^{-1}$ moles of rhodium per mole of olefin in the reactor zone. Concentrations in the range of about $1 \times 10^{-5}$ moles to about $5 \times 10^{-2}$ moles of rhodium per mole of olefin is preferred. Rhodium concentrations in the range of about $1 \times 10^{-4}$ up to $1 \times 10^{-3}$ are most preferred because most efficient utilization of rhodium is obtained while the cost of the rhodium component is maintained within a commercially reasonable amount.

The molar ratios of bidentate ligand to rhodium can vary over a wide range. Typically, the ligand to rhodium ratio will vary within the range of about 1 up to 50. Preferably the molar ratio of ligand to rhodium will vary within the range of 2 up to 30. In a most preferred embodiment, the molar ratio of ligand to rhodium will vary within the range of about 3 up to 20.

In the practice of the present invention, selectivity of linear to branched chain aldehyde products is not significantly affected by the mole ratio of ligand/rhodium. Similarly, the linear to branched chain product ratio is not significantly affected by the additional, optional presence of such monodentate organophosphine ligands as diphenyl benzylphosphine, tribenzylphosphine, and the like. Indeed, it has surprisingly been found that catalyst activity increases as the total ligand/rhodium mole ratio is increased. This increase in catalyst activity occurs in contrast to the trends observed with monodentate organophosphines alone where increasing ligand/rhodium mole ratios tend to reduce catalyst activity.

Olefins contemplated for use in the practice of the present invention include straight chain, branched chain, or cyclic, terminal or internal mono olefins containing in the range of 2 up to 20 carbon atoms and non conjugated polyolefins typically having in the range of 5 up to 5,000 carbon atoms, e.g., polybutadiene, with each of the above optionally containing groups or substituents which do not interfere with the hydroformylation process. Such substituents which do not interfere with the hydroformylation process include:
OH,
OR"; wherein R" is $C_1$ up to $C_{20}$ alkyl, aryl, alkyaryl, aralkyl, or acyl radical,

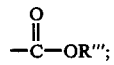

wherein R''' is a $C_1$ up to $C_{20}$ alkyl, aryl, alkaryl or aralkyl radical,

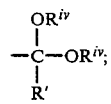

wherein R' is independently selected from H, $C_1$ up to $C_{12}$ alkyl radicals or substituted alkyl radicals, and $C_6$ up to $C_{12}$ aryl radicals or substituted aryl radicals, and each $R^{iv}$ is independently selected from the members defined by R', where the groups can be joined together to form a cyclic acetal or ketal, SR"; wherein R" is as defined above, and

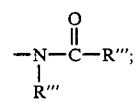

wherein R''' is as defined above.

Substituted derivatives of such olefins and non conjugated polyolefins contemplated for use in practice of the present invention can be represented by the following formulae:

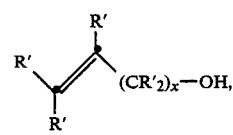

wherein each R' is independently selected from H, $C_1$ up to $C_{12}$ alkyl or alkylene radicals or substituted alkyl or alkylene radicals, and $C_6$ up to $C_{12}$ aryl radicals or substituted aryl radicals; and x is a whole number between 1 and 20;

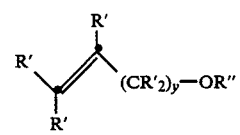

wherein R' is as defined above; R" is $C_1$ up to $C_{20}$ alkyl, aryl, alkaryl, aralkyl or acyl radical, and y is a whole number between 0 and 20;

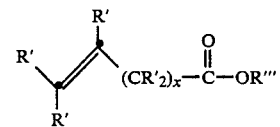

wherein R' and x are as defined above; and R''' is a $C_1$ up to $C_{20}$ alkyl, aryl, alkaryl or aralkyl radical;

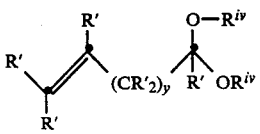

wherein R' and y are as defined above; and each $R^{iv}$ is defined as in R', plus, the two $R^{iv}$ groups may be joined together to form a cyclic acetal or ketal;

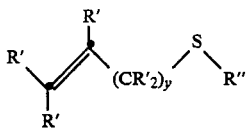

where R', R" and y are as previously defined; and

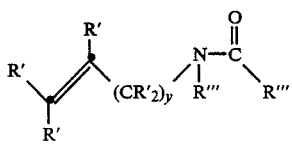

wherein R', R''', and y are as previously defined

Exemplary alpha olefins suitable for use in the practice of the present invention are ethylene, propylene, 1-butene, 2-methylpropylene, 2-methyl-1-butene, 1-pentene, 1-hexene, 1-heptene, 1-octene, 2-ethyl 1-hexene, 1-dodecene and 1-octadecene. Also useful in the practice of the present invention are the internal olefins such as 2-butene and cyclic olefins such as cyclooctene. If desired, mixtures of olefins, particularly ethylene and propylene, can also be fed to the reactor.

Preferred olefins employed in the practice of the present invention contain in the range of 2 up to 10 carbon atoms, with olefins containing in the range of 2 up to 4 carbon atoms being preferred The process of the present invention can be carried out in any suitable reaction vessel. Suitable reaction vessels include gas sparged reactors, liquid overflow reactors, stirred tank reactors, trickle bed reactors, and the like, as are known to those of skill in the art.

A presently preferred reactor for carrying out the process of the present invention with low boiling products is a gas sparged reactor such that the catalyst does not leave the reaction zone with the aldehyde product which is taken overhead by unreacted gases. For higher boiling products, a liquid overflow type of reactor may be more appropriate to facilitate product handling and recovery.

With a gas sparged reactor, the overhead gases are chilled in a vapor/liquid separator to condense out the aldehyde product, with the gases being recycled to the reactor while the liquid product is let down to atmospheric pressure for separation and purification by conventional means. A side draw from the reactor can optionally be provided for more complete product distillation. Small amounts of catalyst are withdrawn from the reactor along with the side draw of reaction medium. Following product recovery, the catalyst can optionally be subjected to appropriate regeneration treatment before being returned to the reactor, following the addition of make up ligand thereto.

The process of the present invention is carried out at temperatures in the range of about 0° up to 190° C. Temperatures in the range of about 50° up to 150° C. are preferred, with temperatures in the range of 75° up to 125° C. being most preferred because reactions at such temperatures give excellent rate of reaction with minimum catalyst deactivation.

Pressures in the range of about 15 up to 1500 psia are typically employed for the hydroformylation reaction. Preferably, reaction pressure in the range of about 100 up to 450 psia are employed, with reaction pressures in the range of about 150 up to 250 psia being most preferred because economically attractive reaction rates are obtained at these relatively low reaction pressures, which in turn reduces the cost of reaction equipment, the need for added compressor capacity, gas recycle, etc.

Hydrogen to carbon monoxide ratios in the reaction zone can vary over a wide range. Typically, hydrogen to carbon monoxide ratios of about 0.5:1 up to 10:1 will be employed. Hydrogen to carbon monoxide ratios in the range of about 1:1 up to 6:1 are preferred, with ratios in the range of about 1.1:1 up to 5:1 being most preferred because high catalyst activity is obtained with minimum by-product formation when reaction is carried out at such ratios.

Contact times employed in the practice of the present invention can vary over a wide range. Reactant residence times in the range of seconds up to hours are operable In terms of total gas flows, reactant space velocities typically fall in the range of 1 up to 1000 standard cubic feet per minute per cubic foot of catalyst (SCF/M/C). Preferably, reactant space velocities in the range of 25 up to 200 SCF/M/C are employed, with reactant space velocities in the range of 50 up to 125 SCF/M/C being most preferred because at such space velocities, with relatively low molecular weight products such as butyraldehyde, a desirable balance is achieved between product production rate and fluid levels in the reaction vessel. At lower gas flow rates, the rate of reaction is limited by the level of reactant gas present in the reaction zone, while at higher gas flow rates, the reactor contents tend to be removed from the vessel faster than the rate of formation of additional product. The preferred gas flow rate with any given olefin feed will be a function of the total reactor pressure, reaction temperature, product production rate, and the like.

It is preferred that the reagents employed for the invention hydroformylation process be substantially free of materials which may reduce catalyst activity or completely deactivate the catalyst. Thus, such materials as conjugated dienes, acetylenes, mercaptans, mineral acids, halogenated organic compounds, and free oxygen should generally be excluded from the reaction. It is of note that no special precautions regarding the exclusion of water need be taken, as small amounts of water have not been found to be detrimental to the invention hydroformylation process.

The invention will now be illustrated further by reference to the following non limiting examples.

EXAMPLES

The reactor employed for the hydroformylation reaction described in the Examples consists of a vertically held stainless steel 4 foot by 1 inch (inside diameter) tube having a stainless steel filter element welded into its side near the bottom. The bottom of the tube has a drain valve and the top has a side port through which the vaporized products and unreacted gases leave the reactor. The top end of the tube is provided with a screwed plug which can be removed for charging the catalyst and which contains a thermowell whereby the temperature of the catalyst solution (reaction medium) in the reactor is measured accurately. Hydrogen and carbon monoxide are fed to the reactor from cylinders via pressure regulators and flow controllers which use differential pressure cells and air actuated flow control valves to maintain precise flow. A third feed of nitrogen from a cylinder goes to the reactor via a pressure regulator and rotameter with needle valve. The carbon monoxide passes through a heated commercial "deoxo" unit as marketed by Engelhard Industries, Division, Engelhard Minerals and Chemicals Corp., Newark, N.J., to remove oxygen impurities. The nitrogen admixed with hydrogen is passed through a similar "deoxo" unit before entering the reactor. Propylene is fed as a liquid to a preheater section or plenum chamber, where it is combined with the other feed gases and is vaporized prior to entering the reactor via the stainless steel filter element. The propylene feed rate is measured using rate-of-level drop in a calibrated tank containing liquid propylene using an armored rotameter with a needle valve to control the liquid propylene feed rate.

In operation, the catalyst is contained as a solution in the lower portion of the reactor tube and the reactant gases are sparged up through the solution as bubbles emanating from the filter element product butyraldehyde is formed in the catalyst solution where it accumulates and eventually is removed as a vapor by vapor/liquid equilibration with unreacted gases. This type of reactor is known as a vapor take off or vapor stripped reactor. The hot gases are cooled upon leaving the reactor through said side port and the butyraldehyde product, along with some unreacted propylene, collects in a cooled high pressure separator connected by suitable conduit means to said side port. The noncondensed gases are let down to atmospheric pressure via a back pressure regulator which controls the reactor pressure. Additional butyraldehyde is condensed out of the atmospheric pressure gas stream by passing it through a series of three dry ice traps. Once an hour the contents of the high pressure separator and dry ice traps are collected and combined. The weight of butyraldehyde product obtained during the hour and its n/iso ratio are calculated using standard gas/liquid chromatographic techniques in combination with the crude weight of the product collected.

In practice, approximately one hour is required for this reaction unit to achieve a regime where catalyst activity and n/iso product ratios to reach substantially constant levels.

EXAMPLE 1

Demonstration of Catalyst Performance

A catalyst charge comprised of 0.0625 gram of rhodium (as rhodium 2-ethylhexanoate) and 1.44 gram of α,α'-bis(diphenylphosphino)-o-xylene dissolved in 0.195 liter of 2,2,4-trimethyl 1,3-pentanediol monoisobutyrate was charged to the reactor system described above. The reactor was maintained under the following conditions:
Experimental Conditions:
$H_2/CO$ ratio - 5:1
$H_2$ flow rate - 5.6 liters/min.
CO flow rate - 1.1 liters/min.
$N_2$ flow rate - 0.96 liter/min.
Propylene gas flow - 1.92 liters/min. (at STP).
Total reaction pressure - 260 psig.
Reaction temperature - 115° C.
The reactor was operated for 6 hours under the conditions set forth above. The catalyst produced aldehydes with a normal to branched isomer ratio of about 2.38/1 at a production rate of about 3.42 pounds of butyraldehyde per gram of rhodium per hour (lb. HBu/g-Rh-hr.).

EXAMPLE 2

Effect of Varying Hydrogen and Carbon Monoxide Partial Pressures

The table below summarizes the results of the use of different partial pressures of hydrogen and carbon monoxide in the reactor feed to change the n/iso isomer product ratio. The runs shown below used the same concentration of rhodium and α,α'-bis-(diphenylphosphino)-o-xylene ligand as in Example 1. The propylene and nitrogen partial pressures in the feed gas were kept constant in the runs and the hydrogen and carbon monoxide flows were varied to adjust their partial pressures.

TABLE 1

Effect of Hydrogen/Carbon Monoxide Ratio on N/Iso Ratio at 115° C. with Rh/α, α'-bis-(diphenylphosphino)-o-xylene Catalyst

| Partial Pressure in Feed, psia | | | $H_2/CO$ Ratio | N/Iso Ratio | Intrinsic Activity, lb. HBu/ g Rh-hr |
|---|---|---|---|---|---|
| $H_2$ | CO | $C_3H_6$ | | | |
| 161 | 31 | 55 | 5.1/1 | 2.38/1 | 3.42 |
| 146 | 49 | 52 | 3/1 | 2.44/1 | 1.91 |
| 96 | 96 | 54 | 1/1 | 2.64/1 | 1.51 |
| 79 | 113 | 56 | 0.7/1 | 2.85/1 | 1.04 |

The results set forth above demonstrate that the normal/iso (or branched) ratio for product aldehyde is increased by greater than 10% by merely varying the $H_2/CO$ ratio.

EXAMPLE 3

Demonstration of Catalyst Stability

A catalyst mixture was prepared from rhodium 2-ethylhexanoate (containing 31.25 mg of Rh, 0.3037 mmole), α,α'-bis(diphenylphosphino)-o-xylene ligand (0.35 gram, 0.73 mmole), and 195 mL of Texanol under nitrogen. This was charged under argon to the bench-scale hydroformylation reactor described in Example 1. The hydroformylation of propylene was carried out at a reactor temperature of 115° C. and total working pressure of 260 psig. The flows to the reactor below are expressed in liters per minute STP: hydrogen 3.36, carbon monoxide 3.36, nitrogen 0.96, and propylene 1.92. The butyraldehyde product was collected hourly and analyzed as described in Example 1. At the end of the working day, the propylene and nitrogen feeds were stopped and the hydrogen and carbon monoxide flows were reduced to 1.0 liter per minute each. The reactor was kept at psig and 115° C. overnight. The following morning, the propylene and nitrogen feeds were started again and the hydroformylation reaction was carried out under the conditions described for the first day. This procedure was repeated such that 4 days of hydroformylation were carried out.

TABLE 2

Four Day Run at 115° C. with Rh/α,α'-
bis(diphenylphosphino)-o-xylene
Catalyst Propylene Hydroformylation

| Day | Catalytic Activity, lb HBu/g Rh-Hr | N/Iso Ratio |
|---|---|---|
| 1 | 1.613 | 2.76 |
| 2 | 1.663 | 2.75 |
| 3 | 1.700 | 2.73 |
| 4 | 1.676 | 2.76 |

The results tabulated in Table 2 demonstrate the ability of this catalyst to hold constant catalytic activity and selectivity to a given n/iso product ratio over a period of time.

EXAMPLE 4

Comparison

These experiments were carried out using the same procedure as Example 3 using chelating ligands not within the scope of this invention. In each of the examples below a catalyst charge was prepared from 31.25 mg of Rh, 0.3037 mmole charged as the 2-ethyl-hexanoate salt, and 0.73 mmole of the chelating ligand dissolved in 195 mL of Texanol under nitrogen. The duration of these runs was 3 days. The data below show a more rapid decline in catalyst activity than was observed with the chelate of this invention.

TABLE 3

Three Day Run at 115° C. with Rh/Trans-1,2-bis-
(diphenylphosphinomethyl)-3,3-dimethylcyclobutane
Catalyst Propylene Hydroformylation

| Day | Catalytic Activity, lb HBu/g Rh-Hr | N/Iso Ratio |
|---|---|---|
| 1 | 2.612 | 4.93 |
| 2 | 2.441 | 4.92 |
| 3 | 2.058 | 4.73 |

TABLE 4

Three Day Run at 115° C. with Rh/Endo,cis-2,3-
bis(diphenylphosphinomethyl[2.2.1]bicycloheptane
Catalyst Propylene Hydroformylation

| Day | Catalytic Activity, lb HBu/g Rh-Hr | N/Iso Ratio |
|---|---|---|
| 1 | 1.06 | 2.93 |
| 2 | 1.02 | 2.99 |
| 3 | 0.79 | 2.49 |

These results demonstrate that bidentate ligands not within the scope of the present invention are not as stable as invention ligands. See, for example, results of Example 3, Table 2.

EXAMPLE 5

Hydroformylation of 1-Octene with
Rhodium-α,α'-bis(diphenylphosphino)-o-xylene and
platinum α,α'-bis(diphenylphosphino)-o-xylene This is an example of the use of this invention with higher alpha olefins.

A 300-mL stainless steel autoclave equipped with a magnetically driven stirrer was charged under nitrogen with rhodium (14.55 mg of rhodium, 0.14 mmole charged as the 2-ethylhexanoate salt), α,α'-bis(diphenylphosphino)-o-xylene ligand (0.16 gm, 0.34 mmole), 1-octene (22.44 grams), and toluene (70 mL). This was pressured to 300 psig with a 1/1 mixture of hydrogen/carbon monoxide (synthesis gas) and heated to 105° C. The autoclave was repressured to 300 psig with the synthesis gas mixture whenever the pressure dropped to 250 Psig. The reaction was kept at 105° C. for 2 hours, during which time a total pressure drop of 460 psig was observed. The mixture was analyzed by gas/liquid chromatography and showed a 94.3 percent conversion of 1-octene. A 90.6 percent yield to isomeric nonanal products was obtained based on 1-octene charged. The ratio of linear/branched nonanal product was 3.47/1.

As a comparison, the reaction of 1-octene with the rhodium α,α'-bis(diphenylphosphino)-o-xylene catalyst was repeated as described in the preceding paragraph, and, as a side by side comparison, prior art system was considered under the same conditions except that the catalyst employed was a combination of α,α'-bis(diphenylphosphino)-o-xylene/-platinum/tin in a molar ratio of 2/1/5. The tin component was charged to the reactor as $SnCl_2 \cdot 2H_2O$, and the platinum was charged as bis(benzonitrile)$PtCl_2$. Results are summarized below:

TABLE 5

| Metal | % of 1 Octene Converted to: | | Linear/Branched Nonanal Ratio |
|---|---|---|---|
| | Isooctenes | Nonanals | |
| Rh | 3.22 | 92.22 | 3.03 |
| Pt | 2.41 | trace | normal nonanal only |

These results demonstrate that the rhodium α,α'-bis(diphenylphosphino)-o-xylene catalyst system is much more effective for olefin hydroformylation than is the prior art Pt-based system. Note that invention hydroformylation produces a desirable mixture of normal and branched chain aldehyde products, while prior art catalyst produces only normal aldehyde. It is also of note that prior art catalyst is much more effective for olefin isomerization than for hydroformylation. Conversely, the invention hydroformylation process produces only a very minor amount of isomerized material.

EXAMPLE 6

These experiments used catalyst charges of 33.45 mg of rhodium (0.325 mmole) charged as the 2-ethylhexanoate and α,α'-bis(diphenylphosphino)-o-xylene ligand (0.77 gram, 1.62 mmole) dissolved in 180 mL of Texanol. Runs 1-14 are propylene hydroformylation runs carried out in the apparatus described in Example 1. The total pressure in the reactor was 260 psig and the reactor temperature was 115° C. In each of the examples the hydrogen, propylene, carbon monoxide, and nitrogen feed rates were varied to cause different partial pressures of these reactants to be present in the feed to the reactor. Runs 1 through 14 show the effects of varying the reactant partial pressures on the catalytic activity of the Rh/α,α'-bis-(diphenylphosphino)-o-xylene catalyst. The data are listed in Table 6. The partial pressures of hydrogen, carbon monoxide, and propylene are recorded as psia and the catalytic activity is expressed as pounds of butyraldehyde per gram of rhodium per hour (lb HBu/g Rh-hr).

TABLE 6

Kinetic Data for 5/1 α,α'-bis(diphenyl-phosphino)-o-xylene/Rh Catalyst at 115° C. in the Hydroformylation of Propylene

| Run No. | Partial Pressure in Feed, psia | | | Catalytic Activity, lb HBu/g Rh-hr |
|---|---|---|---|---|
|  | $H_2$ | CO | $C_3H_6$ |  |
| 1 | 121.8 | 40.7 | 85.1 | 4.35 |
| 2 | 123.5 | 28.6 | 82.2 | 6.78 |
| 3 | 121.5 | 52.2 | 85.3 | 2.86 |
| 4 | 123.0 | 68.8 | 82.9 | 2.20 |
| 5 | 123.3 | 41.2 | 55.0 | 3.07 |
| 6 | 122.7 | 41.0 | 43.8 | 2.47 |
| 7 | 121.8 | 40.7 | 71.3 | 4.57 |
| 8 | 126.8 | 42.4 | 91.1 | 5.34 |
| 9 | 118.2 | 41.5 | 81.0 | 4.67 |
| 10 | 152.2 | 41.5 | 81.0 | 5.32 |
| 11 | 81.8 | 40.3 | 86.4 | 3.94 |
| 12 | 134.2 | 41.2 | 82.5 | 4.26 |
| 13 | 100.4 | 41.2 | 82.5 | 3.63 |
| 14 | 98.6 | 40.5 | 85.9 | 4.42 |

The data in Table 6 were used to derive a power law rate expression that describes the catalytic activity in terms of the reactant partial pressures. The equation below describes the catalytic activity of Rh/OXYL catalyst at 115° C. as a function of the partial pressures of the reactants in the feed in psia to the reactor.

$$\text{Lb HBu/g Rh-Hr} = 1.16 [H_2]^{0.52} [CO]^{-1.38} [C_3H_6]^{0.89}$$

TABLE 7

Effect of α,α'-bis(diphenylphosphino) o-xylene/Rh Mole Ratio on Hydroformylation of Propylene

| Run No. | OXYL/Rh* Mole Ratio | N/Iso Ratio | Catalytic Activity, lb HBu/ g Rh-hr |
|---|---|---|---|
| 15 | 1.2/1 | 2.33/1 | 1.77 |
| 16 | 1.5/1 | 2.28/1 | 2.31 |
| 17 | 2.0/1 | 2.26/1 | 3.20 |
| 18 | 3.5/1 | 2.22/1 | 4.32 |
| 19 | 5.0/1 | 2.27/1 | 4.64 |

*OXYL = α,α'-bis(diphenylphosphino)-o-xylene

The above power rate low expression reflects a surprisingly strong influence of carbon monoxide partial pressure on catalyst activity for a Rh/α,α'-bis(diphenylphosphino)-o-xylene catalyst. In contrast to prior art rhodium based hydroformylation systems, relatively low CO partial pressures are desirable.

EXAMPLE 7

Effect of Varying Ligand/Rhodium Ratio

These experiments show that the mole ratio of α,α'-bis(diphenylphosphino)-o-xylene/Rh in the catalyst has little effect on the selectivity to the linear aldehyde product but increasing mole ratios increase catalytic activity. These examples used 33.45 mg of rhodium charged as the 2-ethylhexanoate salt dissolved in 190 mL of the solvent Texanol. The table below shows the effect of varying the α,α'-bis(diphenylphosphino)-o-xylene/Rh mole ratio in the hydroformylation of propylene at 115° C. The apparatus and general procedure was the same as described in Example 1. The reactant flows used in these examples were: hydrogen 4.31 1/min STP; carbon monoxide 1.44 1/min STP; propylene 2.88 1/min STP; and nitrogen 0.96 1/min STP.

TABLE 7

Effect of α,α'-bis(diphenylphosphino) o-xylene/Rh Mole Ratio on Hydroformylation of Propylene

| Run No. | OXYL/Rh* Mole Ratio | N/Iso Ratio | Catalytic Activity, lb HBu/ g Rh-hr |
|---|---|---|---|
| 15 | 1.2/1 | 2.33/1 | 1.77 |
| 16 | 1.5/1 | 2.28/1 | 2.31 |
| 17 | 2.0/1 | 2.26/1 | 3.20 |
| 18 | 3.5/1 | 2.22/1 | 4.32 |
| 19 | 5.0/1 | 2.27/1 | 4.64 |

*OXYL = α,α'-bis(diphenylphosphino)-o-xylene

These results demonstrate that catalyst activity is surprisingly increased at increased ligand/rhodium ratios without any significant effect on the n/iso product ratio.

EXAMPLE 8

Use of Mixed Monodentate/Bidentate Ligands

The experimental procedure of Example 7 was repeated with a mixture of the chelating ligand α,α'-bis(diphenylphosphino)-o-xylene, and monodentate phosphorus ligands. Table 8 shows the effect of the addition of a monodentate ligand to the invention hydroformylation reaction system at different monodentate/Rh and monodentate plus chelate/Rh mole ratios.

TABLE 8

Addition of Monodentate Ligands to α,α'-bis-diphenylphosphino)-o-xylene/Rh[OXYL/Rh] Catalyst in the Hydroformylation of Propylene at 115° C.

| Run No. | Monodentate Phosphine* | Mole Ratio of Monodentate Phosphine/ Rh | N/Iso Ratio | Catalytic Activity, lb HBu/ g Rh-hr |
|---|---|---|---|---|
| A. 2/1 OXYL/Rh | | | | |
| 17 | — | 0/1 | 2.26 | 3.20 |
| 20 | DP BzP | 3/1 | 2.28 | 3.91 |
| 21 | DP BzP | 6/1 | 2.29 | 4.92 |
| 22 | TBP | 3/1 | 2.27 | 3.53 |
| 23 | TBP | 6/1 | 2.23 | 4.98 |
| B. 2/1 OXYL/Rh** | | | | |
| 24 | — | — | 2.32 | 2.78 |
| 25 | TBP | 6/1 | 2.27 | 4.89 |
| 26 | TCHP | 3/1 | 2.30 | 4.10 |
| 27 | TCHP | 6/1 | 2.31 | 4.30 |
| 28 | TOP | 3/1 | 2.43 | 2.10 |
| 29 | TOP | 6/1 | 2.58 | 1.05 |
| C. 2/1 OXYL/Rh*** | | | | |
| 30 | — | — | 2.45 | 2.94 |
| 31 | OXYL | 5/1**** | 2.40 | 4.28 |
| 32 | TBP | 5/1 | 2.36 | 4.47 |
| 33 | TDCBP | 6/1 | 2.40 | 3.30 |
| 34 | TTBBP | 6/1 | 2.34 | 4.50 |
| 35 | TPP | 6/1 | 2.34 | 5.34 |
| 36 | DPCHP | 6/1 | 2.33 | 4.90 |

TABLE 8-continued

Addition of Monodentate Ligands to α,α'-bis-diphenylphosphino)-o-xylene/Rh[OXYL/Rh] Catalyst in the Hydroformylation of Propylene at 115° C.

| Run No. | Monodentate Phosphine* | Mole Ratio of Monodentate Phosphine/Rh | N/Iso Ratio | Catalytic Activity, lb HBu/g Rh-hr |
|---|---|---|---|---|
| 37 | DPBP | 6/1 | 2.24 | 5.57 |

*OXYL = α,α'-bis(diphenylphosphino)-o-xylene
DPBzP = diphenylbenzylphosphine
TBP = tribenzylphosphine
TCHP = tricyclohexylphosphine
TOP = tri-n-octylphosphine
TDCBP = tris(3,4-dichlorobenzyl)phosphine
TTBBP = tri(4-tert-butylbenzyl)phosphine
TPP = triphenylphosphine
DPCHP = diphenylcyclohexylphosphine
DPBP = diphenyl-n-butylphosphine
**Experimental conditions:
$H_2$/CO ratio = 2.5:1
$H_2$ flow rate = 4.31 liters/min.
CO flow rate = 1.71 liters/min.
$N_2$ flow rate = 0.96 liters/min.
Propylene gas flow = 2.88 liters/min.
Total reaction pressure = 260 psig
Reaction temperature = 115° C.
Reagent charge as in previous runs.
*Experimental conditions were the same as described above under footnote ; catalyst charge was at reduced concentrations of 25 mg Rh in 200 mL of solvent.
****This number is the mole ratio of total OXYL/RH Runs 20 and 21 show that the addition of the monodentate ligand diphenylbenzylphosphine (DPBzP) surprisingly increases the catalytic activity of a catalyst containing 33.45 mg of rhodium without causing any substantial change in the n/iso product ratio when employing a 2.0/1 mole ratio of α,α'-bis(diphenylphosphino)-o-xylene/Rh. Runs 22, 23, 25 and 32 provide a similar demonstration with respect to the benefits of adding the monodentate ligand tribenzylphosphine (TBP) to the α,α'-bis-(diphenylphosphino)-o-xylene/Rh catalyst.

Runs 26 and 27 demonstrate the beneficial effect of adding a relatively sterically hindered monodentate phosphine (tricyclohexylphosphine, TCHP), and Runs 33-37 demonstrate the beneficial effects obtained by addition of other weakly basic and/or sterically hindered phosphine ligands.

In contrast, Runs 28 and 29 demonstrate that strongly basic, non hindered phosphines such as tri-n-octylphosphine (TOP) do not have the desired beneficial impact on overall catalyst activity Summarizing the results presented in Table 8, it is seen that sterically hindered and/or weakly basic phosphines provide enhanced catalyst activity while highly basic, non-hindered phosphines do not appear to enhance catalyst activity.

The invention has been described in detail with reference to particular embodiments thereof. It will be understood, however, that variations and modifications can be effected within the spirit and scope of the invention.

That which is claimed is:

1. A method for the hydroformylation an unsaturated compound to produce an aldehyde, wherein said unsaturated compound is selected from the group consisting of:

$C_2$ up to $C_{20}$ mono olefins, non conjugated polyolefins, and substituted derivatives thereof, wherein the substituted derivatives contain one or more of the substituents selected from the group consisting of:

OH,

OR"; wherein R" is a $C_1$ up to $C_{20}$ alkyl, aryl, alkaryl or aralkyl radical, $$-\overset{O}{\underset{\|}{C}}-OR''';$$

wherein R''' is a $C_1$ up to $C_{20}$ alkyl, aryl, alkaryl or aralkyl radical, $$-\overset{OR^{iv}}{\underset{R'}{\overset{|}{C}}}-OR^{iv};$$

wherein R' is independently selected from H, $C_1$ up to $C_{12}$ alkyl radicals or substituted alkyl radicals, and $C_6$ up to $C_{12}$ aryl radical or substituted aryl radicals, and each $R^{iv}$ is independently selected from the members defined by R', where the $R^{iv}$ groups can be joined together to form a cyclic acetal or ketal, SR"; wherein R" is as defined above, and $$-\overset{O}{\underset{R'''}{\overset{\|}{N}}}-\overset{\|}{C}-R''';$$

wherein R''' is as defined above;

said method comprising contacting at least one of said olefins with a mixture of hydrogen and carbon monoxide in a molar ratio falling in the range of 0.1:1 up to 20:1, and a catalyst comprising rhodium in chemical complex with at least one bidentate ligand having the structure:

$$(R)_n-Ar\begin{array}{c}\diagup x\\ \diagdown y\end{array}\begin{array}{c}R_4\diagdown\phantom{C}\diagup R_3\phantom{C}R_2\\ C-Y\\ \diagup\phantom{C}\diagdown R_1\\ \\ \diagdown\phantom{C}\diagup R_2\\ C-Y\\ \diagup\phantom{C}\diagdown R_1\\ R_4\phantom{CC}R_3\phantom{C}R_1\end{array}$$

wherein
Ar is selected from aromatic ring compounds having 6 up to 14 carbon atoms;
the x bonds and the y bonds are attached to adjacent carbon atoms on the ring structure;
each R, when present as a substituent, is independently selected from alkyl, alkoxy, aryloxy, aryl, aralkyl, alkaryl, alkoxyalkyl, cycloaliphatic, halogen, exclusive of (except Cl, Br or I on the aromatic nucleus on the carbon atom adjacent to the carbon atoms bearing the x or y bonds, alkanoyl, alkanoyloxy, alkoxycarbonyl, formyl, carboxylate moieties, sulfonic acid derivatives, or amino moieties;
n is a whole number in the range of 0–4 where Ar is phenyl; 0–6 where Ar is naphthyl; and 0–8 where Ar is phenanthryl or anthracenyl;
each $R_1$ and $R_2$ is independently selected from alkyl, aryl, aralkyl alkaryl, cycloaliphatic radicals and substituted derivatives thereof;

each $R_3$ and $R_4$ is independently selected from hydrogen and the $R_1$ substituents;

each of the above alkyl groups or moieties is straight or branched chain of 1-20 carbons;

each aryl group contains 6-10 ring carbons;

each cycloaliphatic group contains from 4-8 ring carbons; and each Y is independently selected from the elements P, As, Sb and Bi;

said contacting being carried out in a reaction zone at a temperature in the range of about 20° up to 250° C. and a pressure in the range of about 15 up to 800 psig for a time sufficient for said olefin to react with said synthesis gas to form aldehyde product.

2. The hydroformylation process according to claim 1 wherein each alkyl group or moiety, when present on said bidentate ligand, has in the range of 1-8 carbons.

3. The hydroformylation process according to claim 1 wherein said reaction zone is operated at a temperature in the range of about 80° C. up to 150° C. and at a pressure in the range of about 100 psig up to 400 psig, and the molar ratio of bidentate ligand to rhodium is in the range of about 0.5 up to 200.

4. The hydroformylation process according to claim 3 wherein the total moles of hydrogen and carbon monoxide with respect to moles of said olefin are present in said reaction zone in a ratio in the range of about 0.01 up to 100.

5. A method in accordance with claim 1 wherein the substituted derivatives of said olefins and nonconjugated polyolefins are selected from the group consisting of alcohol of an the structure

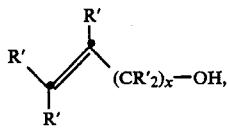

wherein each R' is independently selected from H, $C_1$ up to $C_{12}$ alkyl or alkenyl radicals or substituted alkyl or alkenyl radicals, and $C_6$ up to $C_{12}$ aryl radicals or substituted aryl radicals; and x is a whole number between 1 and 20;

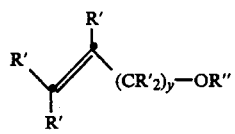

wherein R' is as defined above; R" is $C_1$ up to $C_{20}$ alkyl, aryl, alkaryl, aralkyl or acyl radical, and y is a whole number of 0 up to 20;

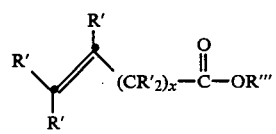

wherein R' and x are as defined above; and R''' is a $C_1$ up to $C_{20}$ alkyl, aryl, alkaryl or aralkyl radical;

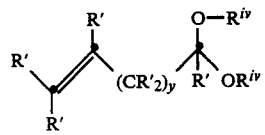

wherein R' and y are as defined above; and each $R^{iv}$ is defined as in R', plus, the two $R^{iv}$ groups may be joined together to form a cyclic acetal or ketal;

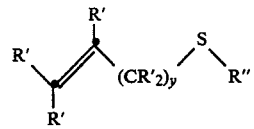

wherein R', R" and y are as previously defined; and

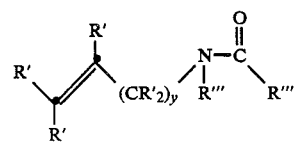

wherein R', R''', and y are as previously defined.

6. The hydroformylation process according to claim 5 wherein said at least one olefin is selected from the group consisting of: ethylene, propylene, 2-methylpropylene, 2-butene, 1-butene, 2-methyl 1-butene, 1-pentene, 1-hexene, 1-heptene, 1-octene, allyl alcohol, allyl acetate, methyl vinyl ether, ethyl vinyl ether, allyl ethyl ether, vinyl acetate, acrolein diethyl acetal, and mixtures of any two or more thereof 7. The hydroformylation process according to claim 1 wherein said rhodium is present in said reaction zone in an amount in the range of about $1 \times 10^{-6}$ up to $1 \times 10^{-1}$ moles per mole of said olefin present in said reaction zone.

8. The hydroformylation process according to claim 1 wherein said bidentate ligand is selected from the group consisting of:
α,α'-bis(diphenylphosphino)-o-xylene,
3,4-dichloro α,α'-bis(diphenylphosphino)-o-xylene,
α,α'-bis[di(p-trifluoromethylphenyl)-phosphino]-o-xylene, and mixtures of any two or more thereof 9. The hydroformylation process of claim 8 wherein said bidentate ligand further comprises at least one monodentate ligand having the structure $PR^v_3$, wherein each $R^v$ is independently selected from alkyl, aryl, aralkyl, alkaryl, cycloaliphatic radicals and substituted derivatives thereof; and wherein substituted derivatives of $R^v$ include substituents selected from the group consisting of alkyl, alkoxy, aryloxy, aryl, aralkyl, alkaryl, alkoxyalkyl, cycloaliphatic, halogen, alkanoyl, alkanoyloxy, alkoxycarbonyl, formyl, carboxylate moieties, sulfonic acid moieties or amino moieties.

10. The hydroformylation process of claim 9 wherein said monodentate ligand is selected from
triphenylphosphine,
tribenzylphosphine,
benzyldiphenylphosphine,
dibenzylphenylphosphine,
tricyclohexylphosphine,
diphenyl cyclohexylphosphine,
diphenyl-n-butylphosphine, tris(3,4-dichlorobenzyl)phosphine, and tri(4-t-butylbenzyl)phosphine.

11. The hydroformylation process according to claim 8 wherein the olefin is propylene.

12. The hydroformylation process according to claim 8 wherein the molar ratio of bidentate ligand to rhodium is in the range of about 1 up to 50.

13. The hydroformylation process according to claim 8 wherein the molar ratio of bidentate ligand to rhodium is in the range of about 2 up to 30.

14. The hydroformylation process according to claim 1 wherein at steady state hydroformylation conditions in said reaction zone the molar ratio of bidentate ligand to Rh falls within the range of about 2 up to 20, the ratio of Rh(mg)/solvent (ml) falls within the range of about 0.07 up to 0.28, the ratio of [olefin feed in L(STP)/min]/mg. of Rh falls within the range of about 0.015 up to 1.50, the ratio of [CO or $H_2$ feed in L(STP)/min]/mg. of Rh Falls within the range of about 0.015 up to 1.5, the temperature is maintained in the range of about 80° C. up to 150° C. and the reactor pressure is maintained in the range of about 240 psig up to 280 psig.

15. The hydroformylation process according to claim 1 wherein said bidentate ligand has the structure:

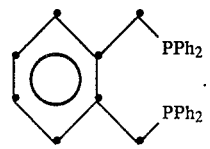

16. The hydroformylation process according to claim 15 wherein the olefin is propylene.

17. The hydroformylation process according to claim 15 wherein the molar ratio of bidentate ligand to rhodium is within the range of about1 up to 50.

18. The hydroformylation process according to claim 15 wherein the molar ratio of bidentate ligand to rhodium is within the range of about 2 up to 30.

19. The hydroformylation process according to claim 15 wherein the olefin comprises a mixture of ethylene and propylene.

* * * * *

UNITED STATES PATENT AND TRADEMARK OFFICE
CERTIFICATE OF CORRECTION

PATENT NO. : 4,960,949

DATED : October 2, 1990

INVENTOR(S) : Thomas J. Devon, Gerald W. Phillips, Thomas A. Puckette, Jerome L. Stavinoha, Jeffrey J. Vanderbilt It is certified that error appears in the above-identified patent and that said Letters Patent is hereby corrected as shown below:

Claim 1, Column 15, Line 60, insert ---of--- after hydroformylation.

Claim 1, Column 16, Line 3, "alkaryl or aralkyl radical," should read ---alkaryl, aralkyl, or acyl radical,---.

Claim 1, Column 16, Line 10, delete "arakyl" and insert ---aralkyl---.

Claim 1, Column 16, Line 17, delete "selected." and insert ---selected---.

Claim 1, Column 16, Line 57, delete "(except".

Claim 5, Column 17, Line 35, "of alcohol of an the structure" should read ---of an alcohol of the structure---.

Claim 5, Column 17, Line 49, before the formula, insert ---a compound of the structure:---.

Claim 5, Column 17, Line 59, before the formula, insert ---an ester of the structure:---.

Claim 5, Column 18, Line 1, before the formula, insert---an acetal and ketal of the structure:--.

Claim 5, Column 18, Line 12, before the formula, insert ---a sulfide of the structure:---.

UNITED STATES PATENT AND TRADEMARK OFFICE
CERTIFICATE OF CORRECTION

PATENT NO. : 4,960,949

DATED : October 2, 1990

INVENTOR(S) : Thomas J. Devon, Gerald W. Phillips, Thomas A. Puckette, Jerome L. Stavinoha, Jeffrey J. Vanderbilt It is certified that error appears in the above-identified patent and that said Letters Patent is hereby corrected as shown below:

Claim 5, Column 18, Line 20, before the formula, insert --an amide of the structure:--.

Claim 14, Column 19, Line 22, delete "Falls" and insert ---falls---.

Signed and Sealed this

Tenth Day of March, 1992

Attest:

HARRY F. MANBECK, JR.

*Attesting Officer*         *Commissioner of Patents and Trademarks*